US000002021H

(19) United States

(12) Statutory Invention Registration (10) Reg. No.: US H2021 H

Hoskins et al. (43) Published: May 7, 2002

(54) PENICILLIN BINDING PROTEIN FROM *STREPTOCOCCUS PNEUMONIAE*

(75) Inventors: JoAnn Hoskins, Indianapolis, IN (US); Stanley Richard Jaskunas, Jr., Natick, MA (US); Genshi Zhao, Indianapolis; Pamela Kay Rockey, Franklin, both of IN (US)

(73) Assignee: Eli Lilly and Company, Indianapolis, IN (US)

(21) Appl. No.: 09/377,465

(22) Filed: Aug. 19, 1999

Related U.S. Application Data

(60) Provisional application No. 60/111,862, filed on Dec. 11, 1998, and provisional application No. 60/100,887, filed on Sep. 23, 1998.

(51) Int. Cl.[7] ..... G01N 33/554; G01N 33/569

(52) U.S. Cl. ..... 435/7.32; 435/71.2

(58) Field of Search ..... 530/350, 356; 435/183, 71.2, 252.33; 424/190.1

(56) References Cited

PUBLICATIONS

Hakenbeck et al (J. Bacteriology, vol. 180, No. 7, pp. 1831–1840, 1998.*

Ellerbrok et al (European Journal of Biochemistry, vol. 144, pp. 637–641, 1984.*

Lehninger (Principles of Biochemistry, Worth Publishers, Inc., New York, NY, Sally Anderson, June Fox, Eds, 1982.*

Potgieter et al (Current Microbiology, vol. 24, pp. 289–294, 1992.*

El Kharroubi et al (Biochemical Journal vol. 280, pp. 63–469, 1991.*

Wu et al (Antimicrobial Agents and Chemotherapy vol. 36(3) pp. 533–539, 1992.*

Reichmann P, Konig A., Linares J., Alcaide F., Tenover FC., McDougal L., Swidsinski S., Hakenbeck R., "A global gene pool for high–level cephalosporin resistance in commensal Streptococcus species and *streptococcus pneumoniae", Journal of Infectious Diseases*, 176(4): 1001–12, (Oct. 1997).

Stingele F., Mollet B., "Disruption of the gene encoding penicillin–binding protein 2b (pbpb) causes altered cell morphology and cease in exopolysaccharide production in *Stretococcus thermophilus* Sfi6", *Molecular Microbiology*, 22(2): 357–66, (Oct. 1996).

Coffey TJ., Dowson CG., Daniels M., Spratt BG., Spratt BG., "Horizontal spread of an altered penicillin–binding protein 2B gene between *Streptococcus pneumoniae* and *Streptococcus oralis", FEMS Microbiology Letters*, 110(3): 335–9, (Jul. 1, 1993).

Martin C., Briese T., Hakenbeck R., "Nucleotide sequences of genes encoding penicillin–binding proteins from *Streptococcus pneumoniae* and *Streptococcus oralis* with high homology to *Escherichia coli* penicillin binding proteins 1a and 1b", Journal of Bacteriology, 174(13): 4517–23, (Jul. 1992).

* cited by examiner

*Primary Examiner*—Charles T. Jordan

*Assistant Examiner*—M. Thomson

(74) *Attorney, Agent, or Firm*—Thomas D. Webster; Raymond S. Parker III; Charles E. Cohen

(57) ABSTRACT

The invention provides isolated nucleic acid compounds encoding a novel high molecular weight PBP of *Streptococcus pneumoniae*. Also provided are vectors and transformed heterologous host cells for expressing the PBP and a method for identifying compounds that bind and/or inhibit the enzymatic activity of the PBP.

2 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

pJAH242
7599 bp pJAH242
7599 bp

PENICILLIN BINDING PROTEIN FROM *STREPTOCOCCUS PNEUMONIAE*

CROSS-REFERENCE

This application claims priority of Provisional Application Serial No. 60/100,887 filed on Sep. 23, 1998 and Provisional Application Serial No. 60/111,862, filed on Dec. 11, 1998.

FIELD OF THE INVENTION

This invention relates to recombinant DNA technology. In particular the invention pertains to the cloning of a gene, pbp-nv2, encoding a novel high molecular weight penicillin binding protein (PBP), PBP-Nv2, from *Streptococcus pneumoniae* and the use of the gene and its encoded protein in a screen for new inhibitors of bacterial cell wall biosynthesis.

BACKGROUND

The emergence of antibiotic resistance in common pathogenic bacterial species has justifiably alarmed the medical and research communities. The emergence and rapid spread of beta-lactam resistance in *Streptococcus pneumoniae* has been particularly problematic. This organism is responsible for many respiratory tract infections, and resistance to beta-lactam drugs has been attributed to a modification of one or more of the penicillin-binding proteins (PBPs). Furthermore, penicillin-resistant *Streptococcus pneumoniae* are frequently resistant to other commonly used antibiotics, such as erythromycin. These multi-drug resistant (MDR) organisms are a real threat to humans, particularly children and the elderly. Increasingly, the only drug that can be used to treat infections with MDR organisms is vancomycin, and there is considerable concern that the bacteria could also develop resistance to vancomycin.

The PBPs are involved in bacterial cell wall synthesis. The cell wall comprises a peptidoglycan layer which provides mechanical rigidity for the bacterium. The peptidoglycan layer is composed of a sugar backbone (alternating residues of N-acetylglucosamine and N-acetylmuramic acid) attached to a pentapeptide (also referred to as "stem peptide") containing D and L amino acid residues. In the formation of the mature peptidoglycan, a lipid-linked disaccharide-pentapeptide is translocated across the cytoplasmic membrane, exposing the pentapeptide sidechains to the cell surface. Transglycosylation of the sugar residues then leads to polymerization of the backbone sugar residues. Further stabilization of the nascent peptidoglycan occurs by a transpeptidation enzymatic reaction that crosslinks adjacent pentapeptide moieties. The high molecular weight PBPs catalyze these final steps in peptidoglycan synthesis. Without the crosslinking step the peptidoglycan structure is severely weakened and susceptible to degradation. Indeed, the crosslinking step constitutes the target of action for antibiotic compounds such as penicillin and other beta-lactam drugs.

When effective as antibiotic agents, beta-lactam drugs interact with PBPs to form an acyl-enzyme intermediate. This intermediate is resistant to hydrolysis. Mechanistically, beta-lactam drugs act as irreversible inhibitors. Resistance to beta-lactam drugs in *Streptococcus pneumoniae* arises through mutation events such that one or more low-affinity "mosaic" PBPs replace a wild-type PBP. The molecular basis of resistance has in a few cases been correlated with specific mutations within a PBP gene. The discovery of new antibacterial compounds against the transpeptidase domain of PBP-Nv2 or to an unexploited target (e.g. the transglycosylase domain) would be particularly useful against *Streptococcus pneumoniae* infections.

SUMMARY OF THE INVENTION

The present invention is designed to meet the aforementioned need and provides, inter alia, isolated nucleic acid molecules that encode a novel PBP from *Streptococcus pneumoniae*. The invention also provides protein products encoded by the gene, in substantially purified form.

Having the cloned pbp-nv2 gene of *Streptococcus pneumoniae* enables the production of recombinant PBP-Nv2 protein and derivatives thereof for the implementation of assays and screens to identify new inhibitory compounds targeted at the peptidoglycan biosynthetic pathway.

In one embodiment the present invention relates to the isolated gene pbp-nv2 that encodes a novel *Streptococcus pneumoniae* PBP, PBP-Nv2,. The gene comprising the nucleotide sequence is identified as SEQ ID NO. 1.

In another embodiment the present invention relates to a novel protein molecule, PBP-Nv2, wherein said protein molecule comprises the sequence identified as SEQ ID NO. 2.

In another embodiment, the present invention relates to a soluble form of PBP-Nv2 (designated PBP-Nv2$^S$) wherein PBP-Nv2$^S$ comprises amino acid residues 85 through 821, inclusive, of SEQ ID NO.2.

In a further embodiment the present invention relates to a ribonucleic acid molecule encoding PBP-Nv2 protein, said ribonucleic acid molecule comprising the sequence identified as SEQ ID NO. 3:

In yet another embodiment, the present invention relates to a recombinant DNA vector that incorporates the *Streptococcus pneumoniae* pbp-nv2 gene in operable linkage to gene expression sequences enabling said PBP gene to be transcribed and translated in a host cell.

In still another embodiment the present invention relates to homologous or heterologous host cells that have been transformed or transfected with a vector carrying the cloned pbp-nv2 gene from *Streptococcus pneumoniae* such that said gene is expressed in the host cell.

In a still further embodiment, the present invention relates to a method for identifying compounds that bind the *Streptococcus pneumoniae* PBP-Nv2 protein or fragment thereof.

DEFINITIONS

Figure 1:
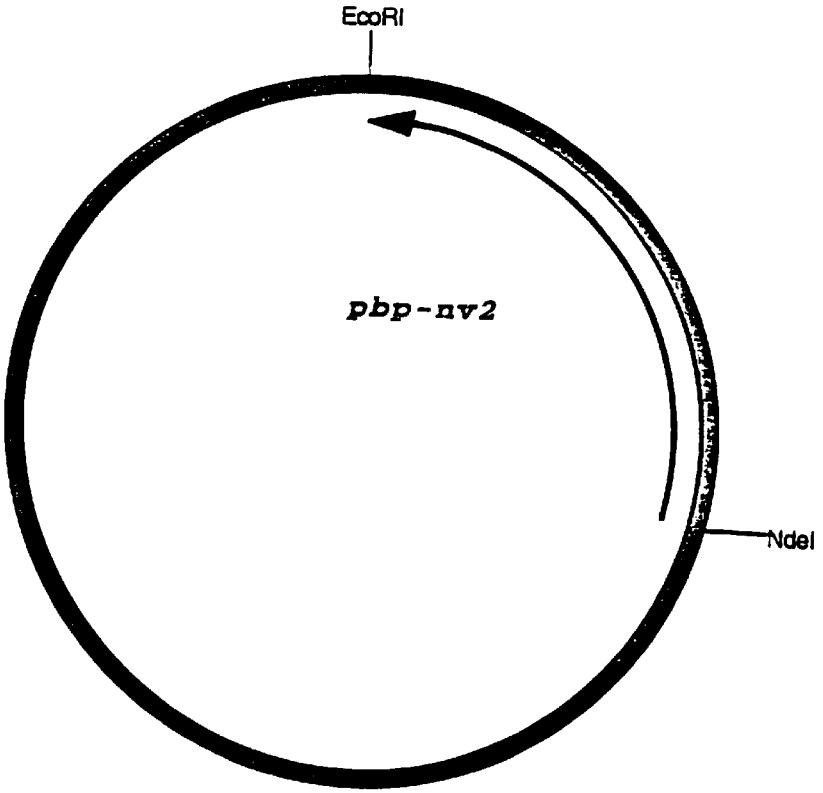
FIG. 1 Plasmid pJAH242, useful for high level expression of the *Streptococcus pneumoniae* pbp-nv2$^S$ gene of the present invention in the heterologous procaryotic host cell *Escherichi coli.*

"PBP" refers generically to a penicillin binding protein.

"PBP-Nv2" refers to the novel high molecular weight PBP from *Streptococcus pneumoniae* that is the subject of this invention and which is specified by SEQ ID NO.2.

"PBP-Nv2$^S$" refers to a soluble form of PBP-Nv2 wherein the membrane spanning region and the cytoplasmic region of PBP-Nv2 have been removed, leaving amino acid residues 85 through 821 of SEQ ID NO.2.

"pbp-nv2" refers to the *Streptococcus pneumoniae* genomic sequence encoding PBP-Nv2.

"pbp-nv2$^S$" refers to a portion of pbp-nv2 that encodes PBP-Nv2$^S$ comprising nucleotide residues 253 through 2466 of SEQ ID NO.1.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

"Functional domain" refers to a region of a protein having one or more distinct biological functions, for example, enzymatic activity, transmembrane anchoring, DNA binding, etc. A functional domain comprises a sequence of amino acids, the length of which and the identity of amino acid residues therein, may or may not be critical to function.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound that hybridizes with another nucleic acid compound.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The term "stringency" refers to hybridization conditions. High stringency conditions disfavor non-homologous base-pairing. Low stringency conditions have the opposite effect. Stringency may be altered, for example, by temperature and salt concentration.

"Transglycosylation" refers to an enzymatic reaction catalyzed by a high molecular weight PBP in which the sugar residues of lipid-linked disaccharide pentapeptide molecules are polymerized during the formation of the peptidoglycan structure of the bacterial cell wall.

"Transpeptidation" refers to an enzymatic reaction catalyzed by a high molecular weight PBP in which the pentapeptide sidechains of lipid-linked disaccharide pentapeptide molecules are cross-linked during the formation of the peptidoglycan structure of the bacterial cell wall.

DETAILED DESCRIPTION

The pbp-nv2gene (SEQ ID NO.1) of the present invention encodes a novel high molecular weight PBP of *Streptococcus pneumoniae* (SEQ ID NO. 2). The pbp-nv2 gene disclosed herein comprises a DNA sequence of 2466 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

The PBP-Nv2 protein defined by SEQ ID NO.2 comprises a membrane-bound protein having several functional domains. At the amino terminal end, amino acid residues from about 1 through 44 of SEQ ID NO.2 define a cytoplasmic domain. The middle portion of the molecule from about amino acid residues 45 through 84 of SEQ ID NO.2, comprises a transmembrane region. At the carboxy terminal end of the molecule, which extends into the extra-cellular environment, amino acid residues from about 85 through 821 of SEQ ID NO.2 comprise a functional domain, wherein resides the transpeptidation (viz. penicillin-binding) and transglycosylase activities.

The PBP-Nv2 protein may be modified by deletion of one or more functional domains. For example, the amino terminal domain and trans-membrane domains may be deleted without a loss of function at the carboxy terminal end (viz. binding of penicillin and transglycosylase activity). A deleted form of the PBP-Nv2 protein lacking the amino terminal and transmembrane regions results in a soluble form of the protein, designated PBP-Nv2$^{S}$.

Gene Isolation Procedures

Those skilled in the art will recognize that the gene of the present invention may be obtained by a plurality of applicable genetic and recombinant DNA techniques including, for example, polymerase chain reaction (PCR) amplification, or de novo DNA synthesis. (See e.g., J. Sambrook et al. *Molecular Cloning,* 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the pbp-nv2 gene of *Streptococcus pneumoniae* comprising the present invention or fragment thereof could be isolated by PCR amplification of *Streptococcus pneumoniae* genomic DNA or cDNA using oligonucleotide primers targeted to any suitable region of SEQ ID NO. 1. Methods for PCR amplification are widely known in the art. See, e.g., *PCR Protocols: A Guide to Method and Application*, Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn.). A positive result is determined by detecting an appropriately-sized DNA fragment following agarose gel electrophoresis.

Protein Production Methods

One embodiment of the present invention relates to the substantially purified protein or fragments thereof encoded by the gene disclosed herein (SEQ ID NO.1).

Skilled artisans will recognize that the protein of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The protein of the present invention can also be produced by recombinant DNA methods using the cloned gene of *Streptococcus pneumoniae* disclosed herein. Recombinant methods are preferred if a high yield is desired. Expression of said cloned gene can be carried out in a variety of suitable host cells well known to those skilled in the art. In a recombinant method the pbp-nv2 or pbp-nv2$^S$ gene is introduced into a host cell by any suitable means, well known to those skilled in the art. While chromosomal integration of the cloned PBP gene is within the scope of the present invention, it is preferred that the gene be cloned into a suitable extra-chromosomally maintained expression vector so that the coding region of the gene is operably linked to a constitutive or inducible promoter.

The basic steps in the recombinant production of PBP-Nv2 or PBP-Nv2$^S$ of the present invention are:

a) constructing a natural, synthetic or semi-synthetic DNA encoding said PBP protein;

b) integrating said DNA into an expression vector in a manner suitable for expressing said PBP protein, as the natural protein product or as a fusion protein;

c) transforming or otherwise introducing said vector into an appropriate eucaryotic or prokaryotic host cell forming a recombinant host cell, d) culturing said recombinant host cell in a manner enabling expression of said protein; and e) recovering and substantially purifying said protein by any suitable means, well known to those skilled in the art.

Expressing Recombinant PBP Proteins in Procaryotic and Eucaryotic Host Cells

In general, procaryotes are used for cloning DNA sequences and for constructing the vectors of the present invention. Procaryotes may also be employed in the production of a novel PBP protein of the present invention. For example, the *Escherichia coli* K12 strain 294 (ATCC No. 31446) is particularly useful for the prokaryotic expression of foreign proteins. Other strains of *E. coli*, bacilli such as *Bacillus subtilis*, enterobacteriaceae such as *Salmonella typhimurium* or *Serratia marcescans*, various Pseudomonas species and other bacteria, such as Streptomyces, may also be employed as host cells in the cloning and expression of the recombinant proteins of this invention.

Promoter sequences suitable for driving the expression of genes in procaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other promoters, such as that from bacteriophage T7, whose nucleotide sequences are generally known, enable one of skill in the art to ligate such promoter sequences to DNA encoding the proteins of the instant invention using linkers or adapters to supply any required restriction sites. Still other promoters are useful for gene expression in *S. pneumoniae* , for example the ami promoter (Claverys, J. P., et al., "Construction and evaluation of new drug-resistance cassettes for gene disruption mutagenesis in *Streptococcus pneumoniae*, using an ami test platform," Gene (1995) 123–128) Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) that cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to procaryotes, a variety of eucaryotic microorganisms such as yeast are suitable host cells. The yeast *Saccharomyces cerevisiae* is the most commonly used eucaryotic microorganism. A number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced PBP-Nv2 and PBP-Nv2$^S$

An expression vector carrying cloned pbp-nv2 or pbp-nv2$^S$ of *Streptococcus pneumoniae* is transformed or transfected into a suitable host cell using standard methods. Cells that contain the vector are propagated under conditions suitable for expression of the encoded PBP. If the gene is under the control of an inducible promoter, suitable growth conditions would incorporate an appropriate inducer. Recombinantly-produced PBP-Nv2$^S$ or PBP-Nv2 protein may be purified from cellular extracts of transformed cells by any suitable means. Recombinantly-produced PBP-Nv2 is expected to be localized in either the host cell membrane or the host cell cytoplasm. As such, PBP-Nv2 is recoverable from cell extracts and cell membranes by any suitable means, well known to those skilled in the art.

In a preferred process for protein purification the gene encoding the PBP of the present invention is modified at the 5' end to incorporate several histidine residues at the amino terminal end of the encoded protein product. The "histidine tag" enables a simplified protein purification method referred to as "immobilized metal ion affinity chromatography" (IMAC), essentially as described in U.S. Pat. No. 4,569,794, which hereby is incorporated by reference. The IMAC method enables rapid isolation of substantially pure protein starting from a crude cellular extract.

Other embodiments of the present invention comprise isolated nucleic acid sequences. As skilled artisans will recognize, owing to the degeneracy of the genetic code the amino acid compounds of the invention can be encoded by a multitude of different nucleic acid sequences. Because these alternative nucleic acid sequences would encode the same amino acid sequences, the present invention further comprises these alternate nucleic acid sequences.

The nucleic acid sequences encoding SEQ ID NO:2, and disclosed subregions therein may be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the pbp-nv2 or related gene sequence pbp-nv2$^S$ could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

In an alternative and preferred methodology, namely PCR, the DNA sequence comprising a portion or all of SEQ ID NO:1 can be generated from *Streptococcus pneumoniae* genomic DNA using suitable oligonucleotide primers complementary to SEQ ID NO:1 or region therein, as described in U.S. Pat. No. 4,889,818, which hereby is incorporated by reference. Suitable protocols for performing the PCR are widely known and are disclosed in, for example, *PCR Protocols: A Guide to Method and Applications*, Ed. Michael A. Innis et al., Academic Press, Inc. (1990).

The ribonucleic acids of the present invention may be prepared using the polynucleotide synthetic methods discussed supra, or they may be prepared enzymatically using RNA polymerase to transcribe a suitable DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of the template to be transcribed. See, J. Sambrook, et al., supra, at 18.82–18.84.

This invention also provides nucleic acids, RNA or DNA, that are complementary to SEQ ID NO:1 or SEQ ID NO:3.

The present invention also provides probes and primers useful for a variety of molecular biology techniques including, for example, hybridization screens of genomic or subgenomic libraries. A nucleic acid compound comprising SEQ ID NO:1, SEQ ID NO:3 or a complementary sequence thereof, or a fragment thereof, and which is at least 18 base pairs in length, and which will selectively hybridize to *Streptococcus pneumoniae* DNA or mRNA encoding the PBP of the present invention, is provided. Preferably, the 18 or more nucleotide bases are DNA. These probes and primers can be prepared by enzymatic methods well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those that comprise DNA. The most preferred recombinant DNA vectors comprise the isolated DNA sequence, SEQ ID NO:1. Plasmid pJAH242 is an especially preferred DNA vector for expressing the soluble form of the PBP of this invention in *E. coli.*

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. The skilled artisan will recognize a number of inducible promoters that respond to a variety of inducers, for example, carbon source, metal ions, heat, and others. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing the extra-cellular export of a resulting polypeptide.

Host cells harboring the nucleic acids disclosed herein are also provided by the present invention. A preferred host is *E. coil* that has been transfected or transformed with a vector that comprises a nucleic acid of the present invention.

The present invention also provides a method for constructing a recombinant host cell capable of expressing SEQ ID NO:2, or the soluble form thereof, said method comprising transforming or otherwise introducing into a host cell a recombinant DNA vector that comprises an isolated DNA sequence which encodes SEQ ID NO:2 or fragment thereof. The preferred host cell is any strain of *E. coli* that can accommodate high level expression of an exogenously introduced gene. Preferred vectors for expression are those which comprise SEQ ID NO:1. An especially preferred expression vector for use in *E. coli* is pJAH242, which comprises nucleotide residues 253 through 2466 of SEQ ID NO:1. (See FIG. 1). Transformed host cells may be cultured under conditions well known to skilled artisans such that a recombinant protein is expressed, thereby producing in the recombinant host cell the PBP of the instant invention.

For the purpose of identifying or developing new antibiotic compounds it is useful to determine compounds that bind to PBPs and/or inhibit the transpeptidase or transglycosylase activity. The instant invention provides a screen for identifying compounds that bind PBP-Nv2 and/or PBP-Nv2$^S$ or fragment thereof, said screen comprising the steps of:

a) preparing and substantially purifying a recombinant PBP of the invention;

b) exposing said PBP to a test compound; and c) monitoring, by any suitable means, the binding by said compound to said PBP, or inhibition of enzymatic activity of said PBP by said compound.

The substrate for a transglycosylase assay can be made according to art-recognized methods (See e.g. DiBerardino et al. FEBS Letters, 392, 184–88 (1996). For example, the lipid precursor substrate can be prepared from *Streptococcus pneumoniae* membranes, or from the membranes of any other suitable bacteria, UDP-Mur-Nac-pentapeptide, and UDP-N-acetyl-[$^{14}$C]glucosamine (Amersham, Buckinghamshire, UK). Transglycosylase activity is measured by the production of the peptidoglycan polymerization product essentially by mixing the substrate with a source of PBP and monitoring the amount of [$^{14}$C]-label in the peptidoglycan.

The above-disclosed screening system could also be used to identify compounds that inhibit the transpeptidase activity of PBP-Nv2 or PBP-Nv2$^S$. In a preferred embodiment of this aspect of the invention compounds are tested for their ability to competitively inhibit the binding of labeled penicillin to PBP-Nv2 or PBP-Nv2$^S$.

The screening system described above provides a means to determine compounds that interact with the PBPs of the present invention and which may interfere with peptidoglycan biosynthesis. This screening method may be adapted to automated procedures such as a PANDEX® (Baxter-Dade Diagnostics) system, allowing for efficient high-volume screening for potential inhibitory agents.

The following examples more fully describe the present invention. Those skilled in the art will recognize that the particular reagents, equipment, and procedures described below are merely illustrative and are not intended to limit the present invention in any manner.

EXAMPLES

Example 1

Construction of a DNA Vector for Expressing *Streptococcus pneumoniae* pbp-nv2$^S$ Gene in a Heterologous Host Plasmid pJAH242 (See FIG. 1) is an approximately 7600 base pair expression vector suitable for expressing a modified pbp-nv2$^S$ in procaryotic host *E. coli*. This plasmid contains an origin of replication (Ori), an ampicillin resistance gene (Amp), useful for selecting cells that have incorporated the vector following a transformation procedure, and further comprises the T7 promoter in operable linkage to the coding region of said PBP gene. Parent plasmid pET16b (obtained from Novogen, Madison, Wis.) is linearized by digestion with endonucleases NdeI and EcoRI. Linearized pET16b is ligated to a DNA fragment bearing NdeI and EcoRI cohesive ends, comprising a modified pbp-nv2$^S$ gene. The pbp-nv2$^S$ gene is ligated into pET16b which contains a region just downstream of the ATG initiation codon that encodes 10 histidine residues followed by a factor Xa cleavage site, Ile-Glu-Gly-Arg (SEQ. ID NO: 4), that enables the IMAC protein purification procedure in order to simplify purification of the encoded protein product and subsequent cleavage by factor Xa to remove the histidine tag, if desired.(See Example 4).

Example 2

Construction of a DNA Vector for Expression of pbp-nv2 in a Heterologous Host The plasmid construction method outlined in Example 1 is followed to construct a vector for expressing PBP-Nv2 in a heterologous host such as *E. coli.*

Example 3

Expression of Streptococcus pneumoniae pbp-nv2$^S$ Gene in *Escherichia coli*

Expression plasmid pJAH242 can be transformed into *E. coli* BL21 (DE3) ($F^-$ ompT[lon]hsdS $r_B^-$ $m_B^-$) using standard methods (See e.g. Sambrook et al. Supra). Transformants, chosen at random are tested for the presence of pJAH242 by agarose gel electrophoresis using quick plasmid preparations. Id. Transformants are grown overnight at 37° C. in LB medium supplemented with 100 $\mu$g/ml ampicillin. The overnight culture is diluted into fresh LB medium and allowed to grow to an O.D.$_{600}$ of 0.4 to 0.6. At that point, expression of the vector-bound pbp-nv2$^S$ gene can be induced by adding 0.4 mM IPTG for a period of 3 hours. The induced-culture is then pelleted by centrifugation in preparation for protein purification (See Example 4).

Example 4

Purification of PBP-Nv2$^S$

The recombinant cell pellet, isolated as described in the last step of Example 3, is resuspended in 60 ml of 20 mM potassium phosphate, pH 7.5. The cells are disrupted by passage through a French press, producing a cell extract that is centrifuged at 150,000×g for 1 hour. The supernatant is loaded onto a 200 ml bed-volume XK50 source-Q column (Pharmacia) equilibrated in 20 mM potassium phosphate, pH 7.5 (buffer A). The column is washed with 500 ml buffer A and eluted with a linear gradient of 0 to 1M KC1 in buffer A. Fractions are pooled, tested for penicillin binding activity, and the fractions showing binding activity are dialyzed overnight at 4° C. against 20 mM potassium phosphate, pH 7 (buffer B). The dialyzed protein sample is applied to a XK26 hydroxyapatite column (60 ml bed volume) equilibrated in buffer B. After washing the column with buffer B, samples are eluted with a linear gradient of 20 mM to 700 mM potassium phosphate, pH 7. Fractions exhibiting penicillin binding activity are pooled and dialyzed against 20 mM Tris, pH 8.

The PBP-Nv2$^S$ protein contained in the pooled fractions can be purified further by immobilized metal ion affinity chromatography (IMAC), essentially as described in U.S. Pat. No. 4,569,794, the entire contents of which is hereby incorporated by reference. Briefly, the IMAC procedure involves adding to the protein sample the following components at the indicated final concentrations: 0.5M NaCl, 5 mM imidazole. The sample is loaded onto a Chelating Sepharose Fast Flow column (Pharmacia, 10 ml bed volume) and the column washed twice with 35 ml each of 20 mM Tris, pH 8, 0.5 M NaCl and 5 mM imidazole; 20 mM Tris, pH 8, 0.5 M NaCl and 60 mM imidazole. The bound protein is eluted from the column with 20 mM Tris, pH 8, 0.5 M NaCl, 1 M imidazole. Six fractions of 3 ml each are collected and tested for penicillin binding activity (See Example 5).

Example 5

Penicillin binds *Streptococcus pneumoniae* PBP-Nv2$^S$

Protein fractions isolated from the IMAC column, as in Example 4, are tested for penicillin binding as follows. About 10 ul of the protein sample eluted from the column is mixed with $^{125}$I-labeled penicillin V at a final concentration of 48 ug/ml. Labeled penicillin is prepared as described in Blaszczak et al. "Radioiododestannylation. Convenient synthesis of a stable penicillin derivative for rapid penicillin binding protein assay," J. Labeled Compd. Radiopharm. 27, 401–06 (1989). About 3 ul of a 1 ug/ul solution of sodium clavulanate is added to prevent degradation of the labeling reagent. The mixture is incubated at 35° C. for 15 minutes. Reactions are terminated by the addition of one-half volume SDS with boiling for 2 minutes. Aliquots of each mixture are fractionated by polyacrylamide gel electrophoresis, and radiolabeled bands are detected by exposure to X-ray film.

This method demonstrates a major labeled band at about 80 kilodaltons (the predicted size of PBP-Nv2$^S$ based on the amino acid sequence shown in SEQ ID NO:2, wherein amino acids 1–84 have been deleted).

Example 6

Determination of PBP-Nv2 Transglycosylase Activity

Radiolabeled lipid precursor for use as substrate is prepared as described in H. Hara and H. Suzuki FEBS Lett. 168, 155–60 (1984). Peptidoglycan synthesis activities are determined in 50 $\mu$l reactions containing 50 mM PIPES, pH 6.1, 10 mM $MgCl_2$, 0.2 mM DTT, 1 mM ATP, 26% DMSO, PBP-Nv2 or PBP-Nv2$^S$ sample and $^{14}$C-labeled lipid precursor. The reaction is incubated for 30 minutes at room temperature and filtered through hydrophilic Durapore PVDF membranes (0.65 $\mu$m; Millipore, Bedford, Mass.). Under these conditions the synthesized peptidoglycan is retained while the unincorporated labeled substrate is washed through using 0.4 M ammonium acetate in methanol. The filter bound radioactivity is determined by scintillation counting.

Example 7

Comparisons of DNA Sequences

The DNA sequence of the entire gene was compared to other known genes that encode penicillin-binding proteins from other strains of Streptococcus in order to identify any differences between this gene and related genes. These regions may be of particular interest in determining specific sections of the gene which may encode differences in the resulting gene product. These differences (so-called mutations) are likely to alter the way the protein interacts with inhibitors or substrates. By this process, it was determined that the previously disclosed DNA sequence of pbp-nv2 contained an undefined nucleotide, specifically an "N" at base number 1009. Further analysis of the data confirmed that that base is, in fact, a guanine residue. In addition, the base at position 280 was changed from an adenine residue to a guanine residue. The amended sequence of the gene is reported in sequence ID 1.

SEQUENCE LISTING

```
<160> NUMBER OF SEQ ID NOS:  4

<210> SEQ ID NO 1
<211> LENGTH: 2466
<212> TYPE: DNA
<213> ORGANISM: Streptococcus pneumoniae
<220> FEATURE:
<221> NAME/KEY: CDS
<222> LOCATION: (1)..(2466)

<400> SEQUENCE: 1

atg caa aat caa tta aat gaa tta aaa cga aaa atg ctg gaa ttt ttc       48
Met Gln Asn Gln Leu Asn Glu Leu Lys Arg Lys Met Leu Glu Phe Phe
  1               5                  10                  15

cag caa aaa caa aaa aat aaa aaa tca gct aga cct ggc aag aaa ggt       96
Gln Gln Lys Gln Lys Asn Lys Lys Ser Ala Arg Pro Gly Lys Lys Gly
             20                  25                  30

tca agt acc aaa aaa tct aaa acc tta gat aag tca gcc att ttc cca      144
Ser Ser Thr Lys Lys Ser Lys Thr Leu Asp Lys Ser Ala Ile Phe Pro
         35                  40                  45
```

-continued

```
gct att tta ctg agt ata aaa gcc tta ttt aac tta ctc ttt gta ctc      192
Ala Ile Leu Leu Ser Ile Lys Ala Leu Phe Asn Leu Leu Phe Val Leu
     50                  55                  60

ggt ttt cta gga gga atg ttg gga gct ggg att gct ttg ggg tac gga      240
Gly Phe Leu Gly Gly Met Leu Gly Ala Gly Ile Ala Leu Gly Tyr Gly
 65                  70                  75                  80

gtg gcc tta ttt gac aag gtt cgg gtg cct cag aca gaa gaa ttg gtg      288
Val Ala Leu Phe Asp Lys Val Arg Val Pro Gln Thr Glu Glu Leu Val
                 85                  90                  95

aat cag gtc aag gac atc tct tct att tca gag att acc tat tcg gac      336
Asn Gln Val Lys Asp Ile Ser Ser Ile Ser Glu Ile Thr Tyr Ser Asp
            100                 105                 110

ggg acg gtg att gct tcc ata gag agt gat ttg ttg cgc act tct atc      384
Gly Thr Val Ile Ala Ser Ile Glu Ser Asp Leu Leu Arg Thr Ser Ile
        115                 120                 125

tca tct gag caa att tcg gaa aat ctg aag aag gct atc att gcg aca      432
Ser Ser Glu Gln Ile Ser Glu Asn Leu Lys Lys Ala Ile Ile Ala Thr
    130                 135                 140

gaa gat gaa cac ttt aaa gaa cat aag ggt gta gta ccc aag gcg gtg      480
Glu Asp Glu His Phe Lys Glu His Lys Gly Val Val Pro Lys Ala Val
145                 150                 155                 160

att cgt gcg acc ttg ggg aaa ttt gta ggt ttg ggt tcc tct agt ggg      528
Ile Arg Ala Thr Leu Gly Lys Phe Val Gly Leu Gly Ser Ser Ser Gly
                165                 170                 175

ggt tca acc ttg acc cag caa cta att aaa cag cag gtg gtt ggg gat      576
Gly Ser Thr Leu Thr Gln Gln Leu Ile Lys Gln Gln Val Val Gly Asp
            180                 185                 190

gcg ccg acc ttg gct cgt aag gcg gca gag att gtg gat gct ctt gcc      624
Ala Pro Thr Leu Ala Arg Lys Ala Ala Glu Ile Val Asp Ala Leu Ala
        195                 200                 205

ttg gaa cgc gcc atg aat aaa gat gag att tta acg acc tat ctc aat      672
Leu Glu Arg Ala Met Asn Lys Asp Glu Ile Leu Thr Thr Tyr Leu Asn
    210                 215                 220

gtg gct ccc ttt ggc cga aat aat aag gga cag aat att gca ggg gct      720
Val Ala Pro Phe Gly Arg Asn Asn Lys Gly Gln Asn Ile Ala Gly Ala
225                 230                 235                 240

cgg caa gca gct gag gga att ttc ggt gta gat gcc agt cag ttg act      768
Arg Gln Ala Ala Glu Gly Ile Phe Gly Val Asp Ala Ser Gln Leu Thr
                245                 250                 255

gtt cct caa gca gca ttt tta gca gga ctt cca cag agt ccc att act      816
Val Pro Gln Ala Ala Phe Leu Ala Gly Leu Pro Gln Ser Pro Ile Thr
            260                 265                 270

tac tct cct tat gaa aat act ggg gag ttg aag agt gat gaa gac cta      864
Tyr Ser Pro Tyr Glu Asn Thr Gly Glu Leu Lys Ser Asp Glu Asp Leu
        275                 280                 285

gaa att ggc tta aga cgg gct aag gca gtt ctt tac agt atg tat cgt      912
Glu Ile Gly Leu Arg Arg Ala Lys Ala Val Leu Tyr Ser Met Tyr Arg
    290                 295                 300

aca ggt gca tta agc aaa gac gag tat tct cag tac aag gat tat gac      960
Thr Gly Ala Leu Ser Lys Asp Glu Tyr Ser Gln Tyr Lys Asp Tyr Asp
305                 310                 315                 320

ctt aaa cag gac ttt tta cca tcg ggc acg gtt aca gga att tca cga     1008
Leu Lys Gln Asp Phe Leu Pro Ser Gly Thr Val Thr Gly Ile Ser Arg
                325                 330                 335

gac tat tta tac ttt aca act ttg gca gaa gct caa gaa cgt atg tat     1056
Asp Tyr Leu Tyr Phe Thr Thr Leu Ala Glu Ala Gln Glu Arg Met Tyr
            340                 345                 350

gac tat cta gct cag aga gac aat gtc tcc gct aag gag ttg aaa aat     1104
Asp Tyr Leu Ala Gln Arg Asp Asn Val Ser Ala Lys Glu Leu Lys Asn
        355                 360                 365
```

-continued

```
gag gca act cag aag ttt tat cga gat ttg gca gcc aag gaa att gaa     1152
Glu Ala Thr Gln Lys Phe Tyr Arg Asp Leu Ala Ala Lys Glu Ile Glu
    370                 375                 380

aat ggt ggt tat aag att act act acc ata gat cag aaa att cat tct     1200
Asn Gly Gly Tyr Lys Ile Thr Thr Thr Ile Asp Gln Lys Ile His Ser
385                 390                 395                 400

gcc atg caa agt gcg gtt gct gat tat ggc tat ctt tta gac gat gga     1248
Ala Met Gln Ser Ala Val Ala Asp Tyr Gly Tyr Leu Leu Asp Asp Gly
                405                 410                 415

aca ggt cgt gta gaa gta ggg aat gtc ttg atg gac aac caa aca ggt     1296
Thr Gly Arg Val Glu Val Gly Asn Val Leu Met Asp Asn Gln Thr Gly
            420                 425                 430

gct att cta ggc ttt gta ggt ggt cgt aat tat caa gaa aat caa aat     1344
Ala Ile Leu Gly Phe Val Gly Gly Arg Asn Tyr Gln Glu Asn Gln Asn
        435                 440                 445

aat cat gcc ttt gat acc aaa cgt tcg cca gct tct act acc aag ccc     1392
Asn His Ala Phe Asp Thr Lys Arg Ser Pro Ala Ser Thr Thr Lys Pro
    450                 455                 460

ttg ctg gcc tac ggt att gct att gac cag ggc ttg atg gga agt gaa     1440
Leu Leu Ala Tyr Gly Ile Ala Ile Asp Gln Gly Leu Met Gly Ser Glu
465                 470                 475                 480

acg att cta tct aac tat cca aca aac ttt gct aat ggc aat ccg att     1488
Thr Ile Leu Ser Asn Tyr Pro Thr Asn Phe Ala Asn Gly Asn Pro Ile
                485                 490                 495

atg tat gct aat agc aag gga aca gga atg atg acc ttg gga gaa gct     1536
Met Tyr Ala Asn Ser Lys Gly Thr Gly Met Met Thr Leu Gly Glu Ala
            500                 505                 510

ctg aac tac tca tgg aat atc cct gct tac tgg acc tat cgt atg ctc     1584
Leu Asn Tyr Ser Trp Asn Ile Pro Ala Tyr Trp Thr Tyr Arg Met Leu
        515                 520                 525

cgt gaa aat ggt gtt gat gtc aag ggt tat atg gaa aag atg ggt tac     1632
Arg Glu Asn Gly Val Asp Val Lys Gly Tyr Met Glu Lys Met Gly Tyr
    530                 535                 540

gag att cct gag tac ggt att gag agc ttg cca atg ggt ggt ggt att     1680
Glu Ile Pro Glu Tyr Gly Ile Glu Ser Leu Pro Met Gly Gly Gly Ile
545                 550                 555                 560

gaa gtc aca gtt gcc cag cat acc aat ggc tat cag acc tta gct aat     1728
Glu Val Thr Val Ala Gln His Thr Asn Gly Tyr Gln Thr Leu Ala Asn
                565                 570                 575

aat gga gtt tat cat cag aag cat gtg att tca aag att gaa gca gca     1776
Asn Gly Val Tyr His Gln Lys His Val Ile Ser Lys Ile Glu Ala Ala
            580                 585                 590

gat ggt aga gtg gtg tat gag tat cag gat aaa ccg gtt caa gtc tat     1824
Asp Gly Arg Val Val Tyr Glu Tyr Gln Asp Lys Pro Val Gln Val Tyr
        595                 600                 605

tca aaa gct act gcg acg att atg cag gga ttg cta cga gaa gtt cta     1872
Ser Lys Ala Thr Ala Thr Ile Met Gln Gly Leu Leu Arg Glu Val Leu
    610                 615                 620

tcc tct cgt gtg aca aca acc ttc aag tct aac ctg act tct tta aat     1920
Ser Ser Arg Val Thr Thr Thr Phe Lys Ser Asn Leu Thr Ser Leu Asn
625                 630                 635                 640

cct act ctg gct aat gca gat tgg att ggg aag act ggt aca acc aac     1968
Pro Thr Leu Ala Asn Ala Asp Trp Ile Gly Lys Thr Gly Thr Thr Asn
                645                 650                 655

caa gac gaa aat atg tgg ctc atg ctt tcg aca cct aga tta acc cta     2016
Gln Asp Glu Asn Met Trp Leu Met Leu Ser Thr Pro Arg Leu Thr Leu
            660                 665                 670

ggt ggc tgg att ggg cat gat gat aat cat tca ttg tca cgt aga gca     2064
Gly Gly Trp Ile Gly His Asp Asp Asn His Ser Leu Ser Arg Arg Ala
```

-continued

```
        675                 680                 685

ggt tat tct aat aac tct aat tac atg gct cat ctg gta aat gcg att     2112
Gly Tyr Ser Asn Asn Ser Asn Tyr Met Ala His Leu Val Asn Ala Ile
    690                 695                 700

cag caa gct tcc cca agc att tgg ggg aac gag cgc ttt gct tta gat     2160
Gln Gln Ala Ser Pro Ser Ile Trp Gly Asn Glu Arg Phe Ala Leu Asp
705                 710                 715                 720

cct agt gta gtg aaa tcg gaa gtc ttg aaa tca aca ggt caa aaa cca     2208
Pro Ser Val Val Lys Ser Glu Val Leu Lys Ser Thr Gly Gln Lys Pro
                725                 730                 735

ggg aag gtt tct gtt gaa gga aaa gag gta gag gtc aca ggt tcg act     2256
Gly Lys Val Ser Val Glu Gly Lys Glu Val Glu Val Thr Gly Ser Thr
            740                 745                 750

gtt acc agc tat tgg gct aat aag tca gga gcg cca gcg aca agt tat     2304
Val Thr Ser Tyr Trp Ala Asn Lys Ser Gly Ala Pro Ala Thr Ser Tyr
        755                 760                 765

cgc ttt gct att ggc gga agt gat gcg gat tat cag aat gct tgg tct     2352
Arg Phe Ala Ile Gly Gly Ser Asp Ala Asp Tyr Gln Asn Ala Trp Ser
    770                 775                 780

agt att gtg ggg agt cta cca act cca tcc agc tcc agc agt tca agt     2400
Ser Ile Val Gly Ser Leu Pro Thr Pro Ser Ser Ser Ser Ser Ser Ser
785                 790                 795                 800

agt agt tct agc gat agc agt aac tca agt act aca cga cct tct tct     2448
Ser Ser Ser Ser Asp Ser Ser Asn Ser Ser Thr Thr Arg Pro Ser Ser
                805                 810                 815

tca agg gcg aga cga taa                                             2466
Ser Arg Ala Arg Arg
            820


<210> SEQ ID NO 2
<211> LENGTH: 821
<212> TYPE: PRT
<213> ORGANISM: Streptococcus pneumoniae

<400> SEQUENCE: 2

Met Gln Asn Gln Leu Asn Glu Leu Lys Arg Lys Met Leu Glu Phe Phe
  1               5                  10                  15

Gln Gln Lys Gln Lys Asn Lys Lys Ser Ala Arg Pro Gly Lys Lys Gly
             20                  25                  30

Ser Ser Thr Lys Lys Ser Lys Thr Leu Asp Lys Ser Ala Ile Phe Pro
         35                  40                  45

Ala Ile Leu Leu Ser Ile Lys Ala Leu Phe Asn Leu Leu Phe Val Leu
     50                  55                  60

Gly Phe Leu Gly Gly Met Leu Gly Ala Gly Ile Ala Leu Gly Tyr Gly
 65                  70                  75                  80

Val Ala Leu Phe Asp Lys Val Arg Val Pro Gln Thr Glu Glu Leu Val
                 85                  90                  95

Asn Gln Val Lys Asp Ile Ser Ser Ile Ser Glu Ile Thr Tyr Ser Asp
            100                 105                 110

Gly Thr Val Ile Ala Ser Ile Glu Ser Asp Leu Leu Arg Thr Ser Ile
        115                 120                 125

Ser Ser Glu Gln Ile Ser Glu Asn Leu Lys Lys Ala Ile Ile Ala Thr
    130                 135                 140

Glu Asp Glu His Phe Lys Glu His Lys Gly Val Val Pro Lys Ala Val
145                 150                 155                 160

Ile Arg Ala Thr Leu Gly Lys Phe Val Gly Leu Gly Ser Ser Ser Gly
                165                 170                 175
```

-continued

```
Gly Ser Thr Leu Thr Gln Gln Leu Ile Lys Gln Gln Val Val Gly Asp
            180                 185                 190

Ala Pro Thr Leu Ala Arg Lys Ala Ala Glu Ile Val Asp Ala Leu Ala
        195                 200                 205

Leu Glu Arg Ala Met Asn Lys Asp Glu Ile Leu Thr Thr Tyr Leu Asn
    210                 215                 220

Val Ala Pro Phe Gly Arg Asn Asn Lys Gly Gln Asn Ile Ala Gly Ala
225                 230                 235                 240

Arg Gln Ala Ala Glu Gly Ile Phe Gly Val Asp Ala Ser Gln Leu Thr
                245                 250                 255

Val Pro Gln Ala Ala Phe Leu Ala Gly Leu Pro Gln Ser Pro Ile Thr
            260                 265                 270

Tyr Ser Pro Tyr Glu Asn Thr Gly Glu Leu Lys Ser Asp Glu Asp Leu
        275                 280                 285

Glu Ile Gly Leu Arg Arg Ala Lys Ala Val Leu Tyr Ser Met Tyr Arg
    290                 295                 300

Thr Gly Ala Leu Ser Lys Asp Glu Tyr Ser Gln Tyr Lys Asp Tyr Asp
305                 310                 315                 320

Leu Lys Gln Asp Phe Leu Pro Ser Gly Thr Val Thr Gly Ile Ser Arg
                325                 330                 335

Asp Tyr Leu Tyr Phe Thr Thr Leu Ala Glu Ala Gln Glu Arg Met Tyr
            340                 345                 350

Asp Tyr Leu Ala Gln Arg Asp Asn Val Ser Ala Lys Glu Leu Lys Asn
        355                 360                 365

Glu Ala Thr Gln Lys Phe Tyr Arg Asp Leu Ala Ala Lys Glu Ile Glu
    370                 375                 380

Asn Gly Gly Tyr Lys Ile Thr Thr Thr Ile Asp Gln Lys Ile His Ser
385                 390                 395                 400

Ala Met Gln Ser Ala Val Ala Asp Tyr Gly Tyr Leu Leu Asp Asp Gly
                405                 410                 415

Thr Gly Arg Val Glu Val Gly Asn Val Leu Met Asp Asn Gln Thr Gly
            420                 425                 430

Ala Ile Leu Gly Phe Val Gly Gly Arg Asn Tyr Gln Glu Asn Gln Asn
        435                 440                 445

Asn His Ala Phe Asp Thr Lys Arg Ser Pro Ala Ser Thr Thr Lys Pro
    450                 455                 460

Leu Leu Ala Tyr Gly Ile Ala Ile Asp Gln Gly Leu Met Gly Ser Glu
465                 470                 475                 480

Thr Ile Leu Ser Asn Tyr Pro Thr Asn Phe Ala Asn Gly Asn Pro Ile
                485                 490                 495

Met Tyr Ala Asn Ser Lys Gly Thr Gly Met Met Thr Leu Gly Glu Ala
            500                 505                 510

Leu Asn Tyr Ser Trp Asn Ile Pro Ala Tyr Trp Thr Tyr Arg Met Leu
        515                 520                 525

Arg Glu Asn Gly Val Asp Val Lys Gly Tyr Met Glu Lys Met Gly Tyr
    530                 535                 540

Glu Ile Pro Glu Tyr Gly Ile Glu Ser Leu Pro Met Gly Gly Gly Ile
545                 550                 555                 560

Glu Val Thr Val Ala Gln His Thr Asn Gly Tyr Gln Thr Leu Ala Asn
                565                 570                 575

Asn Gly Val Tyr His Gln Lys His Val Ile Ser Lys Ile Glu Ala Ala
            580                 585                 590

Asp Gly Arg Val Val Tyr Glu Tyr Gln Asp Lys Pro Val Gln Val Tyr
```

-continued

```
        595                 600                 605

Ser Lys Ala Thr Ala Thr Ile Met Gln Gly Leu Leu Arg Glu Val Leu
    610                 615                 620

Ser Ser Arg Val Thr Thr Thr Phe Lys Ser Asn Leu Thr Ser Leu Asn
625                 630                 635                 640

Pro Thr Leu Ala Asn Ala Asp Trp Ile Gly Lys Thr Gly Thr Thr Asn
                645                 650                 655

Gln Asp Glu Asn Met Trp Leu Met Leu Ser Thr Pro Arg Leu Thr Leu
            660                 665                 670

Gly Gly Trp Ile Gly His Asp Asp Asn His Ser Leu Ser Arg Arg Ala
        675                 680                 685

Gly Tyr Ser Asn Asn Ser Asn Tyr Met Ala His Leu Val Asn Ala Ile
    690                 695                 700

Gln Gln Ala Ser Pro Ser Ile Trp Gly Asn Glu Arg Phe Ala Leu Asp
705                 710                 715                 720

Pro Ser Val Val Lys Ser Glu Val Leu Lys Ser Thr Gly Gln Lys Pro
                725                 730                 735

Gly Lys Val Ser Val Glu Gly Lys Glu Val Glu Val Thr Gly Ser Thr
            740                 745                 750

Val Thr Ser Tyr Trp Ala Asn Lys Ser Gly Ala Pro Ala Thr Ser Tyr
        755                 760                 765

Arg Phe Ala Ile Gly Gly Ser Asp Ala Asp Tyr Gln Asn Ala Trp Ser
    770                 775                 780

Ser Ile Val Gly Ser Leu Pro Thr Pro Ser Ser Ser Ser Ser Ser Ser
785                 790                 795                 800

Ser Ser Ser Ser Asp Ser Ser Asn Ser Ser Thr Thr Arg Pro Ser Ser
                805                 810                 815

Ser Arg Ala Arg Arg
            820
```

<210> SEQ ID NO 3
<211> LENGTH: 2466
<212> TYPE: RNA
<213> ORGANISM: Streptococcus pneumoniae

<400> SEQUENCE: 3

```
augcaaaauc aauuaaauga auuaaaacga aaaaugcugg aauuuuucca gcaaaaacaa     60

aaaaauaaaa aaucagcuag accuggcaag aaagguucaa guaccaaaaa aucuaaaacc    120

uuagauaagu cagccauuuu cccagcuauu uuacugagua uaaaagccuu auuuaacuua    180

cucuuuguac ucgguuuucu aggaggaaug uugggagcug ggauugcuuu gggguacgga    240

guggccuuau uugacaaggu ucgggugccu cagacagaag aauuggugaa ucaggucaag    300

gacaucucuu cuauuucaga gauuaccuau ucggacggga cggugauugc uuccauagag    360

agugauuugu ugcgcacuuc uaucucaucu gagcaaauuu cggaaaaucu gaagaaggcu    420

aucauugcga cagaagauga acacuuuaaa gaacauaagg guguaguacc caaggcggug    480

auucgugcga ccuuggggaa auuuguaggu uuggguuccu cuaguggggg uucaaccuug    540

acccagcaac uaauuaaaca gcaggugguu ggggaugcgc cgaccuuggc ucguaaggcg    600

gcagagauug uggaugcucu ugccuuggaa cgcgccauga auaaagauga gauuuuaacg    660

accuaucuca auguggcucc cuuuggccga aauaauaagg gacagaauau ugcaggggcu    720

cggcaagcag cugagggaau uuucggugua gaugccaguc aguugacugu uccucaagca    780

gcauuuuuag caggacuucc acagaguccc auuacuuacu cuccuuauga aaauacuggg    840
```

-continued

```
gaguugaaga gugaugaaga ccuagaaauu ggcuuaagac gggcuaaggc aguucuuuac    900
aguauguauc guacaggugc auuaagcaaa gacgaguauu cucaguacaa ggauuaugac    960
cuuaaacagg acuuuuuacc aucgggcacg guuacaggaa uuucacgaga cuauuuauac   1020
uuuacaacuu uggcagaagc ucaagaacgu auguaugacu aucuagcuca gagagacaau   1080
gucuccgcua aggaguugaa aaaugaggca acucagaagu uuuaucgaga uuuggcagcc   1140
aaggaaauug aaaauggugg uuauaagauu acuacuacca uagaucagaa aauucauucu   1200
gccaugcaaa gugcgguugc ugauuauggc uaucuuuuag acgauggaac aggucgugua   1260
gaaguaggga augucuugau ggacaaccaa acaggugcua uucuaggcuu uguagguggu   1320
cguaauuauc aagaaaauca aaauaaucau gccuuugaua ccaaacguuc gccagcuucu   1380
acuaccaagc ccuugcuggc cuacgguauu gcuauugacc agggcuugau gggaagugaa   1440
acgauucuau cuaacuaucc aacaaacuuu gcuaauggca auccgauuau guaugcuaau   1500
agcaagggaa caggaaugau gaccuuggga gaagcucuga acuacucaug gaauaucccu   1560
gcuuacugga ccuaucguau gcuccgugaa aauggugguug augucaaggg uuauauggaa   1620
aagaugggguu acgagauucc ugaguacggu auugagagcu ugccaauggg ugugguauu   1680
gaagucacag uugcccagca uaccaauggc uaucagaccu uagcuaauaa uggaguuuau   1740
caucagaagc augugauuuc aaagauugaa gcagcagaug guagaguggu guaugaguau   1800
caggauaaac cgguucaagu cuauucaaaa gcuacugcga cgauuaugca gggauugcua   1860
cgagaaguuc uauccucucg ugugacaaca accuucaagu cuaaccugac uucuuuaaau   1920
ccuacucugg cuaaugcaga uuggauuggg aagacuggua caaccaacca agacgaaaau   1980
auguggcuca ugcuuucgac accuagauua acccuaggug gcuggauugg gcaugaugau   2040
aaucauucau ugucacguag agcagguuau ucuaauaacu cuaauuacau ggcucaucug   2100
guaaaugcga uucagcaagc uuccccaagc auuuggggga acgagcgcuu ugcuuuagau   2160
ccuaguguag ugaaaucgga agucuugaaa ucaacagguc aaaaaccagg gaagguuucu   2220
guugaaggaa aagagguaga ggucacaggu ucgacuguua ccagcuauug ggcuaauaag   2280
ucaggagcgc cagcgacaag uuaucgcuuu gcuauuggcg gaagugaugc ggauuaucag   2340
aaugcuuggu cuaguauugu ggggagucua ccaacuccau ccagcuccag caguucaagu   2400
aguaguucua gcgauagcag uaacucaagu acuacacgac cuucuucuuc aagggcgaga   2460
cgauaa                                                              2466
```

```
<210> SEQ ID NO 4
<211> LENGTH: 4
<212> TYPE: PRT
<213> ORGANISM: Unknown Organism
<220> FEATURE:
<223> OTHER INFORMATION: Description of Unknown Organism: Thrombin
      Cleavage Site

<400> SEQUENCE: 4

Ile Glu Gly Arg
```

60

We claim:

1. An isolated Penicillin Binding Protein $Nv2^S$ from *Streptococcus pneumoniae* consisting of amino acid residues 85 through 821 of SEQ ID NO:2.

2. An isolated Penicillin Binding Protein $Nv2^S$ from *Streptococcus pneumoniae* consisting essentially of amino acid residues 85 through 821 of SEQ ID NO:2.

* * * * *